United States Patent [19]
Kanno et al.

[11] Patent Number: 5,847,231
[45] Date of Patent: Dec. 8, 1998

[54] SELECTIVE NITRATION OF PHENOL DERIVATIVES

[75] Inventors: Hideki Kanno; Hiroyuki Chida; Yurie Otani, all of Koshigaya, Japan

[73] Assignee: Junsei Chemical Co., Ltd., Tokyo, Japan

[21] Appl. No.: 838,672

[22] Filed: Apr. 9, 1997

[30] Foreign Application Priority Data

Aug. 23, 1996  [JP]  Japan .................................. 8-240000

[51] Int. Cl.$^6$ ................................................. C07C 205/00
[52] U.S. Cl. ............................................ 568/706; 568/709
[58] Field of Search ..................... 568/706, 709

[56] References Cited

U.S. PATENT DOCUMENTS 5,414,148  5/1995  Metivier et al. ..................... 568/706

FOREIGN PATENT DOCUMENTS 743851  6/1970  Belgium ............................... 260/126

OTHER PUBLICATIONS

Bischoff et al. Chem. Ber., 35: 3443–3450, 1902.
Arjeh Galum et. al. J. Hetj. Chem., 16:221–224, Mar. 1979.
C.A. Bischoff et al., "Uber Oxalsaurearylester," *Chemische Berichte* 35:3443–3452 (1902) (English language translation).

*Primary Examiner*—Gary Geist
*Assistant Examiner*—J. Parsa
*Attorney, Agent, or Firm*—Testa, Hurwitz & Thibeault, LLP

[57] ABSTRACT

Process for preparing 4-nitrophenol derivatives of formula (IV) with high selectivity, which comprises converting phenols to diphenyl oxalate derivatives of formula (III) and conducting nitration reaction and hydrolysis to give said 4-nitrophenol derivatives.

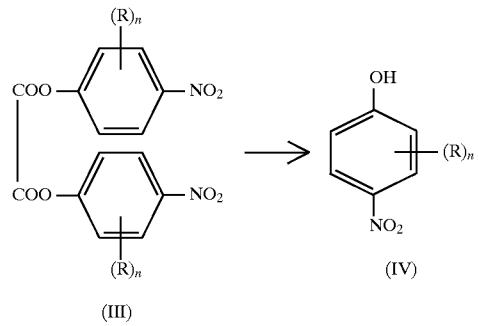

In the above formulae,

R is, the same or different from each other, an alkyl group having 1 to 4 carbon atoms; a halogen atom; an alkoxy group having 1 to 4 carbon atoms; a formyl group; a nitrile group; —COOR$^1$ (R$^1$ is an alkyl group having 1 to 4 carbon atoms); —CONR$^2$R$^3$ (R$^2$ and R$^3$ are, the same or different from each other, hydrogen atom(s) or alkyl group(s) having 1 to 4 carbon atoms); or —COR$^4$ (R$^4$ is an alkyl group having 1 to 4 carbon atoms), and R is not substituted at the 4-position of the phenyl ring and not substituted at the 2- and 6-positions of the phenyl ring at the same time, and, n is 1, 2 or 3.

14 Claims, No Drawings

SELECTIVE NITRATION OF PHENOL DERIVATIVES

BACKGROUND OF THE INVENTION

1. Field of the Invention

The present invention relates to a process for preparing 4-nitrophenol derivatives which are useful intermediates to produce various compounds usable as medicaments, and, more particularly, to a process for preparing 4-nitrophenol derivatives in high selectivity, which comprises converting phenols to diphenyl oxalate derivatives and conducting nitration reaction and hydrolysis to give 4-nitrophenol derivatives.

2. Description of the Prior Art

4-Nitrophenol derivatives such as 5-hydroxy-2-nitrobenzaldehyde, 5-hydroxy-2-nitrobenzoic acid and 5-hydroxy-2-nitrobenzonitrile are useful as intermediates for preparing various physiologically active compounds. Heretofore, 4-nitrophenol derivatives have been prepared by direct nitration reaction of the corresponding phenols, or by first converting the phenols to phenyl carbonates by reaction with poisonous phosgene and subsequently conducting nitration reaction.

Regarding the direct nitration of phenol derivatives, for example Lilli S. Hornig reported the two-phase nitration using concentrated nitric acid in benzene (J.Am. Chem. Soc.,74, 4572–4577 (1952)), and Molcolm J. Thompson and Petrus J. Zeegers also reported the two-phase nitration in dichloromethane as organic solvent (Tetrahedron, 46(7), 2661–2674 (1990)). Thompson et al. reported that the two-phase nitration of phenols yielded a mixture of three kinds of isomers, i.e., 2-nitro, 4-nitro and 6-nitro isomers which were present in similar ratio. They conducted the two-phase nitration of phenol derivatives having various substituent groups at the 3-position, and determined the ratio of the isomers by gas chromatography and/or $^1$H-NMR analysis. The results are shown in the following table.

TABLE

|  | R | 2-Nitro | 4-Nitro | 6-Nitro | Total | (½ o):p |
|---|---|---|---|---|---|---|
| 1. | H | 27.5 | 41.3 | 27.5 | 96.3 | 0.66 |
| 2. | Me | 22.5 | 41.0 | 27.9 | 91.4 | 0.62 |
| 3. | Et | 20.5 | 41.4 | 29.9 | 91.8 | 0.61 |
| 4. | t-But | 19.3 | 40.7 | 34.8 | 94.5 | 0.66 |
| 5. | OH | — | — | — | — | — |
| 6. | OMe | 8.0 | 30.0 | 49.0 | 87.0 | 0.95 |
| 7. | F | 17.0 | 31.0 | 37.8 | 85.8 | 0.88 |
| 8. | Cl | 20.2 | 34.7 | 28.7 | 83.6 | 0.70 |
| 9. | CN | 22.0 | 32.5 | 22.9 | 77.4 | 0.69 |
| 10. | CHO | 22.6 | 38.4 | 25.2 | 86.0 | 0.62 |
| 11. | COMe | 24.9 | 40.3 | 28.7 | 93.9 | 0.66 |
| 12. | NO$_2$ | 8.5 | 21.0 | 17.4 | 46.9 | 0.62 |

The above table shows that the (½ o):p value, i.e., the ratio of the ortho nitro isomers (2-nitro and 6-nitro isomers) to the para nitro isomer (4-nitro isomer) is 0.6–0.95, and therefore it is suggested that the ortho nitro isomers are predominantly produced by the two-phase nitration of phenol derivatives.

For example, in Case No. 9 of the above table, the yield of the para nitro isomer (4-nitro isomer), i.e., 5-hydroxy-2-nitrobenzonitrile, is 32.5%, and in Case No. 10 the yield of the para nitro isomer, i.e., 5-hydroxy-2-nitrobenzaldehyde, is 38.47%. Studies have been done in order to separate a single objective nitrated product from such an isomeric mixture. For example, Hornig reported that 5-hydroxy-2-nitrobenzaldehyde in purified form was obtained in 34% yield by recrystallization from water after direct nitration of 3-hydroxybenzaldehyde in benzene. The present inventors followed this procedure, but could not achieve the objective of obtaining the pure product in such a high yield.

On the other hand, Thompson et al. conducted the direct nitration of 3-cyanophenol and separated the three nitrated isomers from the mixture using silica gel column chromatography. The yields were 21.3% for the 2-nitro isomer (3-hydroxy-2-nitrobenzonitrile), 30.5% for the 4-nitro isomer (5-hydroxy-2-nitrobenzonitrile), and 24.3% for the 6-nitro isomer (3-hydroxy-4-nitrobenzonitrile). Thus, there has been no means other than silica gel column chromatography to separate a single objective product in high purity and high yield after direct nitration of phenol derivatives. The procedure using silica gel column chromatography, however, is uneconomical and low in productivity, and therefore unsuitable for a large-scale commercial production.

Other references disclose preparation of 5-hydroxy-2-nitrobenzaldehyde from 3-hydroxybenzaldehyde by first esterifying the starting compound using phosgene to prepare bis(3-formylphenyl) carbonate, then by subjecting this carbonate to nitration reaction and then hydrolysis (Frederick A. Mason: J. Chem. Soc., 127: 1197–1199, 1925; Martha E. Smith et al.,: J. Am. Chem. Soc., 68: 1301–1303, 1946; Arjeh Galun et al.,: J. Het. Chem., 16: 221–224, 1979).

According to Mason, the yields of the products obtained in the above esterification, nitration and hydrolysis steps were 90%, 97%, and 95%, respectively. A dark brown crystalline product was obtained in the hydrolysis step, which he crystallized several times from 10% aqueous alcohol to obtain purified 5-hydroxy-2-nitrobenzaldehyde having a melting point of 167° C.

In a similar study, Smith et al. reported that they attained 97% yield in the nitration step and also 97% yield in the hydrolysis step. They subjected the crude product in glistening tan crystals (m.p.: 164°–167° C.) to recrystallization from ethanol-water to obtain purified 5-hydroxy-2-nitrobenzaldehyde having a melting point of 163°–166° C. And, Galun et al. reported a 73% total yield of crude 5-hydroxy-2-nitrobenzaldehyde (m.p.: 132° C.) through the nitration and hydrolysis steps.

Thus, it have been well known that converting phenols to phenyl carbonate by using phosgene and subjecting the carbonate to nitration and then hydrolysis can produce para-nitrophenol derivatives with good selectivity. However, phosgene is poisonous and its transfer in a gas cylinder, etc. is prohibited. Therefore, the process may only be carried out in a specifically equipped factory capable of preparing phosgene. This has hindered simple and convenient nitration of phenols to selectively prepare the para-nitrophenol derivatives.

Instead of phosgene, Mason proposed use of ethyl chlorocarbonate in his same reference mentioned above. He converted 3-hydroxybenzaldehyde to ethyl 3-formylphenyl carbonate by reaction with ethyl chlorocarbonate, and nitrated the compound to obtain crude ethyl 3-formyl-4-nitrophenyl carbonate in 96% yield. He says the crude nitration product seems to consist of at least 50% of 4-nitro isomeride. Although he reports that crude 5-hydroxy-2-nitrobenzaldehyde was obtained in a yellow, crystalline precipitate in 41% yield by hydrolysis of the nitrated phenyl carbonate, there is no description of the melting point or the purity of this product. In view of the character of this compound, it is impossible to attain 41% yield of a high-purity product separated from the crude mixture containing about 50% of the 4-nitro isomer. Therefore, assuming the content of the 4-nitro isomer to be about 50%, it is considered that the nitration of ethyl phenyl carbonate gives para-nitrophenol derivatives in only a little higher selectivity as compared with direct nitration of phenols in view of the results shown in the above table.

Under the circumstances, there has been a strong demand for development of a process of nitrating phenols to obtain 4-nitrophenol derivatives in high selectivity.

SUMMARY OF THE INVENTION

An object of the present invention is to provide a process for preparing 4-nitrophenol derivatives safely, simply, conveniently, in high selectivity, in high yield and in high purity.

In more detail, the present invention provides a process for preparing a 4-nitrophenol derivative represented by the following formula (IV):

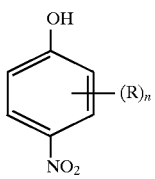

by selective nitration procedure which comprises:
(A) reacting a phenol derivative of the following formula (I):

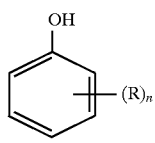

with oxalic acid or a reactive derivative thereof, to give a diphenyl oxalate derivative of the following formula (II):

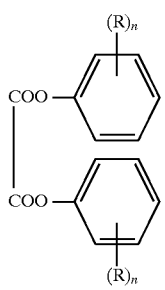

(B) nitrating the derivative of formula (II) to give a bis(4-nitrophenyl) oxalate derivative of the following formula (III):

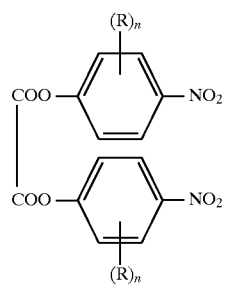

and (C) hydrolyzing the derivative of formula (III) to give said 4-nitrophenol derivative of formula (IV).
[In each formula above, R is, the same or different from each other, an alkyl group having 1 to 4 carbon atoms; a halogen atom; an alkoxy group having 1 to 4 carbon atoms; a formyl group; a nitrile group; —COOR$^1$ (R$^1$ is an alkyl group having 1 to 4 carbon atoms); —CONR$^2$R$^3$ (R$^2$ and R$^3$ are, the same or different from each other, hydrogen atom(s) or alkyl group(s) having 1 to 4 carbon atoms); or —COR$^4$ (R$^4$ is an alkyl group having 1 to 4 carbon atoms), n is 1, 2 or 3, and it should be noted that R is not substituted at the 4-position of the phenyl ring and not substituted at the 2- and 6-positions of the phenyl ring at the same time.]

Another object of the present invention is to provide a process for preparing a diphenyl oxalate derivative of formula (II) by reacting a phenol derivative of formula (I) with an oxalyl halide or oxalic acid.

A further object of the present invention is to provide a process for preparing a bis(4-nitrophenyl) oxalate derivative of formula (III) by reacting a diphenyl oxalate derivative of formula (II) with a nitration reagent selected from the group consisting of a mixture of concentrated sulfuric acid and nitric acid; nitric acid; fuming nitric acid; alkali metal salt of nitric acid in concentrated sulfuric acid; nitrous acetyl; nitronium salt; and nitric oxide.

In a preferred embodiment, the present invention provides a process for preparing a 4-nitrophenol derivative of formula (IV), which comprises (A) reacting a phenol derivative of formula (I) with an oxalyl halide to give a diphenyl oxalate derivative of formula (II), (B) reacting this oxalate derivative of formula (II) with a mixture of concentrated sulfuric acid and nitric acid to give a bis(4-nitrophenyl) oxalate derivative of formula (III), and (C) hydrolyzing the derivative of formula (III) to give said 4-nitrophenol derivative of formula (IV).

DETAILED DESCRIPTION OF THE INVENTION

Heretofore, there is only one report regarding nitration of diphenyl oxalate derivatives such as diguaiacol oxalate and diphenyl oxalate (C. A. Bischoff and A. von Hedenström: Chem. Ber., 35: 3443–3452, 1902). In the report, Bischoff et al. describe that the product obtained by nitration of diguaiacol oxalate was found to be a di-nitrated product of diguaiacol oxalate by the elementary analysis and that the melting point was 225°–235° C. There is no description, however, regarding the position where the two nitro groups were introduced, or what compound was actually obtained in purified form in what yield. Regarding nitration of diphenyl oxalate, they describe that the 4-nitrophenyl oxalate produced by reaction of 4-nitrophenol with oxalic acid and phosphorus oxychloride was identified with the main product produced by nitration of diphenyl oxalate. From the words "main product (Hauptproduct)" in the above description, it is suggested that a by-product, i.e., each ortho-nitro isomer was also produced by this nitration reaction. It is unknown, however, what is the ratio of the para-nitro/ortho-nitro isomers in the produced oxalate.

Under the circumstances, from the description of Bischoff et al. it cannot be predicted that the nitration of phenyl oxalate derivatives would selectively give the para-nitrophenol derivatives.

The paper was published in 1902 and the abstract appears in Beilsteins Handbuch der Organischen Chemie, a world-famous encyclopedia of organic chemistry. However, heretofore no attempts have been made to selectively obtain para-nitro compounds by nitration of phenyl oxalate.

According to the procedures of Thompson et al. mentioned before, the direct nitration of a phenol derivative, e.g., guaiacol, produced only an isomeric mixture in the para/ortho ratio of 37%:58% (analysis by gas chromatography).

Different from these prior art references, the present invention provides a process for selectively obtaining para-nitro compounds by nitrating various phenyl oxalate derivatives and then hydrolyzing the nitrated phenyl oxalates.

Therefore, these prior art references are not a bar for the inventive step of the present invention.

In the present specification, the term "alkyl group having 1 to 4 carbon atoms" stands for a straight-chained or branched-chain alkyl group and may inclide, for example; methyl, ethyl, n-propyl, iso-propyl, n-butyl, iso-butyl, sec-butyl, tert-butyl and the like.

The term "alkoxy group having 1 to 4 carbon atoms" stands for an alkyl substituted oxy group, in which the "alkyl" group has the same meaning as above, and may include, for example, methoxy, ethoxy, n-propoxy, iso-propoxy, n-butoxy, iso-butoxy, sec-butoxy, tert-butoxy and the like.

Accordingly, the "nester group" represented by the formula: $-COOR^1$ may include, for example, methoxycarbonyl, ethoxycarbonyl, n-propoxycarbonyl, iso-propoxycarbonyl, n-butoxycarbonyl, iso-butoxycarbonyl, sec-butoxycarbonyl, tert-butoxycarbonyl and the like; while the "amido group" represented by the formula: $-CONR^2R^3$ may include, for example, aminocarbonyl, mono-methylaminocarbonyl, di-methylaminocarbonyl, mono-ethylcarbonyl, di-ethylaminocarbonyl, methylethylaminocarbonyl, mono-n-propylaminocarbonyl, mono-n-butylaminocarbonyl, methyl-n-butylaminocarbonyl and the like.

The "acyl group" represented by the formula: $-COR^4$ may include, for example, acetyl, propionyl, butyryl and the like.

"Halogen atom" may be chlorine, bromine, fluorine or iodine.

The process of the present invention is described in detail in the following.

1. Esterification:

The process for selectively preparing 4-nitro-phenol derivatives according to the present invention starts with preparation of the diphenyl oxalate derivative of formula (II) by esterifying the phenol derivative of formula (I).

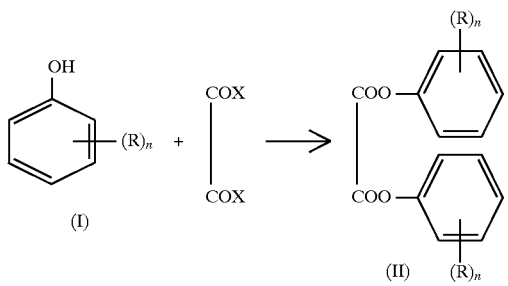

(In the formulae, R and n have the meanings as mentioned before, and X is a halogen atom.)

The R of the starting compound of formula (I) is 1 to 3 groups selected from among those mentioned before, and where n is 2 or 3, the groups are the same or different from each other. The position of the group(s) may be anywhere other than the 4-position of the phenyl ring, and where n is 2 or 3, the R groups are not present at the 2- and 6-positions at the same time. Accordingly, the phenol derivative may be 2- or 3-monosubsituted phenol where n is 1; 2,3-, 2,5- or 3,5-disubstituted phenol where n is 2; and 2,3,5-trisubstituted phenol where n is 3.

The diphenyl oxalate derivative of formula (II) can be obtained by reaction of the phenol derivative of formula (I) with a reactive derivative of oxalic acid, for example, an oxalyl halide such as oxalyl choride, in a suitable organic solvent in the presence of a base as an acid capture reagent.

The organic solvent may be a solvent inert in the reaction, for example, ether solvent such as diethyl ether, tetrahydrofuran, dioxane and the like; hydrocarbon solvent such as benzene, toluene, xylene, cyclohexane and the like; halogenated hydrocarbon solvent such as dichloromethane, dichloroethane, tri-chloroethane, chloroform and the like; ester solvent such as ethyl acetate and the like; dimethylformamide, acetonitrile, dimethylsulfoxide, and so on. Among those, ethyl acetate is preferable.

The base as an acid capture reagent may be an organic base, for example, tri-(lower)alkylamine such as trimethylamine, triethylamine and N,N-diisopropyl-N-ethylamine, pyridine, 4-dimethylaminopyridine and so on.

The reaction may also be carried out in pyridine alone as a base without a solvent.

And, the reaction may also be carried out by means of a conventional procedure for esterification, for example, reacting the phenol derivative of formula (I) with oxalic acid in the-presence of an acid catalyst in an azeotropic solvent (e.g., benzene) under refluxing, and then separating the resulting water; reacting the phenol derivative in the presence of a condensation reagent such as dicyclohexylcarbodiimide (DCC) in such a suitable solvent as mentioned before; or heating together with phosphorus oxychloride in the manner as described by Bischoff et al.

The diphenyl oxalate derivative of formula (II) is thus obtained in quantative yield.

2. Nitration:

The next step is to prepare the bis(4-nitrophenyl) oxalate derivative of formula (III) by nitration reaction of the diphenyl oxalate derivative of formula (II) obtained above.

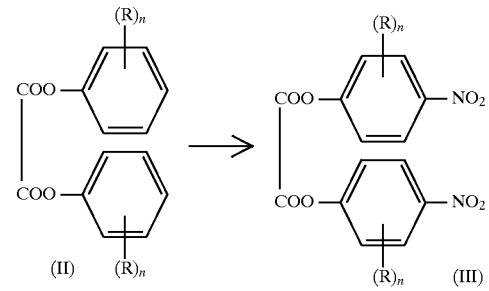

(In the formulae, R and n have the same meanings as above.)

The nitration reaction can be carried out by using a conventional reagent such as a mixture of concentrated sulfuric acid and nitric acid; nitric acid; fuming nitric acid; alkali metal salt of nitric acid in concentrated sulfuric acid; nitronium salt (e.g., nitronium trifluoro-methanesulfonate, nitronium tetrafluoroborate, etc.); and nitric oxide, among which a mixture of concentrated sulfuric acid and nitric acid is most preferable.

The reaction is carried out by mixing the compound of formula (II) with the above-mentioned reagent. The reaction temperature may vary in a wide range from −20° C. to 40° C., preferably from −10° C. to 20° C., and more preferably from −5° C. to 5° C.

After the nitration reaction, the reaction mixture is suspended in ice water, then the resulting precipitate is collected and washed with water to give the bis(4-nitrophenyl) oxalate derivative of formula (III).

The compound of formula (III) may be purified in conventional manner; however, the wet precipitate may be used for the next hydrolysis step without purification. This is advantageous especially for large-scale commercial production.

Some compounds obtained in this nitration step have two nitro groups substituted at the ortho- and para-positions of the phenyl ring when the amount of nitric acid in the mixture of concentrated sulfuric acid and nitric acid ranges from 1 to 2 equivalent mole(s) based on the compound of formula (II) and the reaction temperature is relatively low, for example 0° C.–5° C. Therefore, the present invention also provides a simple and convenient process for preparing 2,4-dinitrophenol derivatives of the compound of formula (I).

3. Hydrolysis:

This step is to prepare the objective 4-nitro-phenol derivative of formula (IV) from the bis(4-nitro-phenyl) oxalate derivative of formula (III) obtained above.

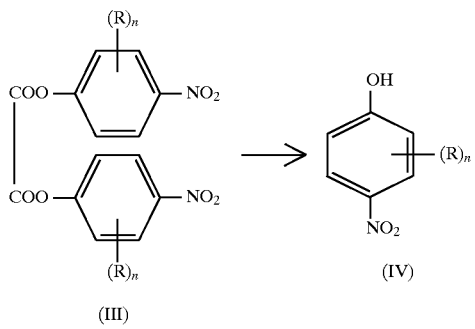

(In the formulae, R and n have the same meanings as above.)

This hydrolysis reaction can be carried out as follows: the compound of formula (III) obtained above in the form of a wet precipitate is subjected to (A) heating together with an excess alkali solution, or (B) mixing for several hours with excess alcohol such as methanol, ethanol, iso-propanol and the like at a room temperature to cause hydrolysis in part and alcoholysis in the other part, to give the 4-nitrophenol derivative of formula (IV).

The alkali solution usable in this hydrolysis reaction may be an alkali metal hydroxide solution such as sodium hydroxide and potassium hydroxide solution. The concentration of the alkali solution may be from 10% to 45%, preferably from 20% to 40%, and more preferably about 35%.

Hydrolysis of the compound of formula (III) by mixing for several hours with excess alcohol such as methanol, ethanol, iso-propanol and the like at a room temperature may preferably be carried out in the presence of acid. Use of methanol in the presence of acid is especially preferable.

Accordingly, in a preferable embodiment the present invention provides a process for preparing the 4-nitrophenol derivative of formula (IV) by selective nitration procedure which comprises:

(A): esterifying the phenol derivative of formula (I) by reaction with an oxalyl halide such as oxalyl chloride to give the diphenyl oxalate derivative of formula (II);

(B): nitrating the thus-obtained derivative of formula (II) by reaction with a mixture of concentrated sulfuric acid and nitric acid to give the bis(4-nitrophenyl) oxalate derivative of formula (III); and, (C): hydrolyzing the thus-obtained derivative of formula (III) by mixing it with excess methanol in the presence of acid.

For example, when 3-hydroxybenzaldehyde as a phenol derivative is nitrated according to the direct nitration procedure of Thompson et al., the isomer ratio calculated in accordance with Case No. 10 of the table shown before is as follows:

2-nitro isomer: 26.2%
4-nitro isomer: 44.5%
6-nitro isomer: 29.2%

On the other hand, according to the process of the present invention, the ratio of the isomers in the crude product is the following, as mentioned later in Example 1:

2-nitro isomer: 0.4%
4-nitro isomer: 99.6%
6-nitro isomer: not detected

This shows that the process of the present invention has high selectivity toward the 4-nitro isomer.

When phenol derivatives are nitrated, nitro groups are generally introduced at both the ortho and para positions of the phenyl ring. According to the process of the present invention, however, the nitro group can be introduced selectively at the para position. The reason seems that the electron density is high at the para position and low at the ortho position in view of the resonance structure of di-ester derivatives of oxalic acid, rather than the steric hindrance at the ortho position.

This was suggested from the experiment results which showed an extremely low reactivity at the ortho position, and, it is also supported by the fact that when one nitro group is introduced at the para position, the electron resonance structure is changed to elevate the electron density at the ortho position and therefore a second nitro group may be introduced there easily.

From these findings, it is predicted that, for other aromatic electrophile substitution reactions, too, e.g., halogenation, sulfonation, acylation, etc., of phenol derivatives, the para position would be selectively substituted by way of reaction via di-ester derivatives of oxalic acid.

The following Examples and Comparative Example illustrate the present invention in more detail. The present invention, however, is not limited to those Examples.

EXAMPLE 1

Preparation of 5-Hydroxy-2-nitrobenzaldehyde a) Esterification 50.06 g (0.41 mol) of 3-hydroxybenzaldehyde was dissolved in 300 ml of ethyl acetate in a four-necked vessel having 500 ml capacity. To this mixture solution 79.4 ml (0.57 mol) of triethylamine was added under nitrogen gas atmosphere and ice-cooling, then, 31.7 g (0.25 mol) of oxalyl chloride was further added dropwise at 5° C. The mixture solution was stirred until disappearance of 3-hydroxybenzaldehyde was confirmed by thin-layer chromatography. When the reaction was over, the reaction mixture was warmed to a room temperature and the resulting precipitate was collected by filtration, washed with water and ethyl acetate to remove triethylamine hydrochloride, and dried in vacuum to give 56.63 g (yield: 92.8%) of bis(3-formylphenyl) oxalate as a light brown solid. m.p.: 163°–166° C.

b) Nitration and Hydrolysis 125 ml of concentrated sulfuric acid was put in a four-necked vessel having 300 ml capacity and stirred under ice-cooling. Then 31.27 g (0.10 mol) of bis(3-formylphenyl) oxalate obtained above was gradually added at 5° C. To this solution a mixture of 40.3 g of concentrated sulfuric acid and 36.0 g of nitric acid (d=1.42) was added dropwise at the same temperature. After being stirred for 3 hours at the same temperature, the reaction mixture was gradually suspended in 600 g of ice water. The resulting precipitate was collected by filtration and washed with water to give a light brown solid. The solid was suspended in 115 ml of methanol, and the suspension was stirred overnight at a room temperature to give a reddish brown solution. This solution mostly comprised 5-hydroxy-2-nitrobenzaldehyde dimethyl acetal. After treatment with a small amount of activated carbon, the solvent was removed and the residue was dissolved in 70 ml of water, then stirred until the completion of hydrolysis of acetal was confirmed by HPLC. The pH of the solution was adjusted to 4 with a 35% sodium hydroxide solution and the mixture was cooled to 5° C. The resulting precipitate was collected by filtration to give a light brown cake.

This cake comprised 5-hydroxy-2-nitrobenzaldehyde, 3-hydroxy-2-nitrobenzaldehyde and 3-hydroxy-4-nitrobenzaldehyde in the HPLC peak area ratio of 99.6:0.4:0, respectively.

Then, only one recrystallization gave 23.32 g (yield: 66.5%) of 5-hydroxy-2-nitrobenzaldehyde as light brown crystals (m.p.: 199.4° C.). No ortho isomer was observed in the crystals by HPLC analysis.

EXAMPLE 2

Preparation of 2-Hydroxy-5-nitrobenzaldehyde a) Esterification 10.14 g (78.87 mmol) of 2-hydroxybenzaldehyde (salicylaldehyde) and 60 ml of ethyl acetate were put in a four-necked vessel having 100 ml capacity, and mixed under nitrogen gas atmosphere. Then 16.8 ml (122.3 mmol) of triethylamine was added under ice-cooling. To this mixture 6.60 g (52.43 mmol) of oxalyl chloride was added dropwise at 5° C. When the reaction was over, the resulting precipitate was collected by filtration, washed with water and ethyl acetate to remove the triethylamine hydrochloride, and dried in vacuum to give 1.37 g (11.6%) of bis(2-formylphenyl) oxalate as a brown solid. m.p.: 134°–135° C.

b) Nitration and Hydrolysis 5 ml of concentrated sulfuric acid was put in a four-necked vessel having 100 ml capacity and stirred under ice-cooling. Then 1.35 g (4.52 mmol) of bis(2-formylphenyl) oxalate obtained above was gradually added at 4° C. or below to give a dark brown solution. To this solution a mixture of 1.82 g of concentrated sulfuric acid and 1.63 g of nitric acid (d=1.42) was added dropwise at 5° C. to 10° C. The reaction mixture was stirred for 3 hours and suspended in 20 g of ice, then the resulting precipitate was collected by filtration and washed with water. The precipitate thus obtained was suspended in 20 ml of methanol, and the suspension was stirred to give a yellow solution. After removal of the solvent, the residue was dissolved in 10 ml of water and the pH of the solution was adjusted to 4 with a 35% sodium hydroxide solution, then the mixture was cooled to 5° C. The resulting precipitate was collected by filtration and washed with water to give 0.56 g (apparent yield: 74.1%) of crude 2-hydroxy-5-nitrobenzaldehyde. This product comprised 2-hydroxy-5-nitrobenzaldehyde and 2-hydroxy-3-nitrobenzaldehyde in the HPLC peak area ratio of 84.3% and 15.7%, respectively. Then 500 mg of this crude product was recrystallized from water to give 370 mg (27.5 %) of 2-hydroxy-5-nitrobenzaldehyde. m.p.: 126°–127° C.

EXAMPLE 3

Preparation of Methyl 5-Hydroxy-2-Nitrobenzoate a) Esterification 10.77 g (70.79 mmol) of methyl 3-hydroxybenzoate and 40 ml of ethyl acetate were put in a four-necked vessel having 100 ml capacity and mixed under nitrogen gas atmosphere. Then 13.8 ml (99.10 mmol) of triethylamine was added under ice-cooling. To this mixture 6.74 g (53.09 mmol) of oxalyl chloride was added dropwise at 5° C. When the reaction was over, the resulting precipitate was collected by filtration, washed with water and ethyl acetate, and dried in vacuum to give 11.79 g (92.9%) of bis(3-methoxycarbonylphenyl) oxalate as light brown crystals. m.p.: 194°–195° C.

b) Nitration and Hydrolysis 20 ml of concentrated sulfuric acid was put in a four-necked vessel having 100 ml capacity, and 5.07 g (14.14 mmol) of bis(3-methoxycarbonylphenyl) oxalate obtained above was gradually added to give a dark brown solution. To this solution a mixture of 5.70 g of concentrated sulfuric acid and 5.09 g of nitric acid (d=1.42) was added dropwise at 5° C. to 10° C. After being stirred for 3 hours, the reaction mixture was suspended in 100 g of ice and the resulting precipitate was collected by filtration and washed with water. The precipitate thus obtained was suspended in 20 ml of methanol, and the suspension was stirred to give a reddish brown solution. After treatment with a small amount of activated carbon, the solvent was removed and the resulting residue was dissolved in 10 ml of water. The pH of the solution was adjusted to 4 with a 35% sodium hydroxide solution and the mixture was cooled to 5° C. The resulting precipitate was collected by filtration and washed with water to give 4.53 g (apparent yield: 82.1%) of crude methyl 5-hydroxy-2-nitrobenzoate. This product comprised methyl 5-hydroxy-2-nitrobenzoate, methyl 3-hydroxy-2-nitrobenzoate and unidentifiable substance in the HPLC peak area ratio of 75.8%, 5.7%, and 18.5%, respectively. Accordingly, the ratio of the para isomer to the ortho isomer was 93:7.

1 g of this crude product was purified by silica gel column chromatography (n-hexane/ethyl acetate=10:1–8:1) to give 830 mg (67.2%) of methyl 5-hydroxy-2-nitrobenzoate. m.p.: 104°–106° C.

EXAMPLE 4

Preparation of 5-Hydroxy-2-Nitrobenzonitrile a) Esterification 7.17 g (60.19 mmol) of 3-hydroxybenzonitrile and 40 ml of ethyl acetate were put in a four-necked vessel having 100 ml capacity and mixed under nitrogen gas atmosphere. Then 8.53 g (84.26 mmol) of triethylamine was added under ice-cooling. To this mixture 4.58 g (36.11 mmol) of oxalyl chloride was added dropwise, and when the reaction was over, the resulting precipitate was collected by filtration, washed with water and ethyl acetate, and dried in vacuum to give 8.80 g (88.0%) of bis(3-cyanophenyl) oxalate as light brown crystals. m.p.: 187°–190° C.

b) Nitration and Hydrolysis 20 ml of concentrated sulfuric acid was put in a four-necked vessel having 100 ml capacity, to which 5.01 g (14.14 mmol) of bis(3-cyanophenyl) oxalate obtained above was gradually added at 0° C. to give a dark brown solution. Then, a mixture of 5.60 g of concentrated sulfuric acid and 5.00 g of nitric acid (d=1.42) was added dropwise at 5° C.

to 10° C. After being stirred for 3 hours, the reaction mixture was suspended in 80 g of ice and the resulting precipitate was collected by filtration and washed with water. The precipitate thus obtained was suspended in 60 ml of methanol and the suspension was stirred to give a reddish brown solution. After treatment with a small amount of activated carbon, the solvent was removed and the resulting residue was dissolved in 10 ml of water. The pH of the solution was adjusted to 4 with a 35% sodium hydroxide solution and the mixture was cooled to 5° C. The resulting precipitate was collected by filtration and washed with water to give 1.28 g (apparent yield: 30.6%) of crude 5-hydroxy-2-nitrobenzonitrile. This product comprised 5-hydroxy-2-nitrobenzonitrile, 3-hydroxy-2-nitrobenzonitrile and di-nitro isomer in the HPLC peak area ratio of 63.75%, 7.37%, and 26.80%, respectively.

1 g of this crude product was purified by silica gel column chromatography (n-hexane/ethyl acetate=10:1) to give 850 mg (23.7%) of 5-hydroxy-2-nitrobenzonitrile. m.p.: 200°–202° C.

EXAMPLE 5

Preparation of 2-Methoxy-4-Nitrophenol a) Esterification 12.70 g (0.1 mol) of 2-methoxyphenol and 75 ml of ethyl acetate were put in a four-necked vessel having 100 ml capacity and mixed therein. Under nitrogen gas atmosphere and ice-cooling, 19.9 ml (0.14 mol) of triethylamine was added. Then 7.77 g (0.06 mol) of oxalyl chloride was added dropwise at 5° C., and the reaction mixture was stirred until disappearance of 2-methoxyphenol was confirmed by thin-layer chromatography. When the reaction was over, the reaction mixture was warmed to a room temperature and the resulting precipitate was collected by filtration, washed with water and ethyl acetate to remove triethylamine hydrochloride, and dried in vacuum to give 10.69 g (yield: 77.2%) of bis(2-methoxyphenyl) oxalate as light brown crystals. m.p.: 123°–126° C.

b) Nitration and Hydrolysis 15 ml of concentrated sulfuric acid was put in a four-necked vessel having 100 ml capacity and ice-cooled. Then 5.02 g (16.16 mmol) of bis(2-methoxyphenyl) oxalate obtained above was added at 5° C. To this solution a mixture of 3.35 g of concentrated sulfuric acid and 2.99 g of nitric acid (d=1.42) was added dropwise at 0° C. The reaction mixture was suspended in 50 g of ice, extracted with chloroform, and dried. After removal of the solvent, the resulting precipitate was collected by filtration to give light brown crystals. The crystals thus obtained were suspended in 20 ml of methanol and the suspension was stirred overnight to give an orange-colored solution. Methanol was removed and the residue was dissolved in 10 ml of water. The pH of the solution was adjusted to 4 with a sodium hydroxide solution and the mixture was ice-cooled. The resulting precipitate was collected by filtration to give 0.64 g of crude crystals.

The HPLC peak area ratio of the isomers in the crude product was as follows:

2-methoxy-4-nitrophenol: 36.4%

2-methoxy-4,6-dinitrophenol: 63.6%

2-methoxy-6-nitrophenol: not detected

The crude crystals were purified by silica gel column chromatography to give 2-methoxy-4-nitrophenol. m.p.: 104° C.

c) Dinitration and Hydrolysis 16 ml of concentrated sulfuric acid was put in a four-necked vessel having 100 ml capacity and ice-cooled. Then 4.55 g (15.05 mmol) of bis(2-methoxyphenyl) oxalate obtained above was added at 5° C. To this solution a mixture of 6.07 g of concentrated sulfuric acid and 5.40 g of nitric acid (d=1.42) was added dropwise at 0° C. The reaction mixture was suspended in 80 g of ice. By filtration and washing with water, a light brown precipitate was obtained. The precipitate was suspended in 20 ml of methanol and the suspension was stirred overnight to give an orange-colored solution. Methanol was removed and the residue was dissolved in 10 ml of water. The pH of the solution was adjusted to 4 with a sodium hydroxide solution and the mixture was ice-cooled. The resulting precipitate was collected by filtration to give 0.54 g (8.7%) of 2-methoxy-2,4-dinitrophenol as yellow crystals. m.p.: 68°–70° C.

IR (KBr): 3436, 1542, 1284 cm$^{-1}$

NMR (DMSO-d$_6$) δ: 7.7–8.2 (dd, Ph, 2H), 3.9 (s, Me, 3H)

EXAMPLE 6

Preparation of 3-Bromo-4-Nitrophenol a) Esterification 10.31 g (59.59 mmol) of 3-bromophenol and 60 ml of ethyl acetate were put in a four-necked vessel having 100 ml capacity and mixed therein. To this mixture 11.6 ml (83.43 mmol) of triethylamine was added under nitrogen gas atmosphere and ice-cooling. Then 4.53 g (37.75 mmol) of oxalyl chloride was added dropwise at 5° C., and the mixture was warmed to a room temperature. The resulting precipitate was collected by filtration, washed with water and ethyl acetate to remove triethylamine hydrochloride, and dried in vaccum to give 1.27 g of bis(3-bromophenyl) oxalate as light brown crystals. On the other hand, the ethyl acetate layer was separated from the filtrate, then washed and dried. The solvent was removed in vacuum and the residue was washed with methanol to remove the starting material, i.e., 3-bromophenol, and dried to give 2.06 g of bis(3-bromophenyl) oxalate. Total amount: 3.33 g (yield: 28.0%)

b) Nitration and Hydrolysis 12 ml of concentrated sulfuric acid was put in a four-necked vessel having 100 ml capacity and ice-cooled. Then 3.22 g (8.05 mmol) of bis(3-bromophenyl) oxalate obtained above was added at 5° C. To this solution a mixture of 3.25 g of concentrated sulfuric acid and 2.90 g of nitric acid (d=1.42) was added dropwise at 0° C. The reaction mixture was suspended in 20 g of ice and the resulting precipitate was collected. The precipitate thus obtained was suspended in 20 ml of methanol, and the suspension was stirred overnight to give an orange-colored solution. The solvent was removed and the residue was dissolved in 10 ml of water. The pH of the solution was adjusted to 4 with a 35% sodium hydroxide solution and the mixture was ice-cooled. The resulting precipitate was collected by filtration to give 3.51 g (apparent yield: 37.3%) of crude product.

The HPLC peak area ratio of the isomers in the crude product was as follows:

3-bromo-4-nitrophenol: 57.6%

2,4-dinitro-5-bromophenol: 36.0%

2-bromophenol: 6.4%

This crude product was purified by silica gel column chromatography (toluene/ethyl acetate=3:2) to give 3-bromo-4-nitrophenol. m.p.: 130°–135° C.

IR (KBr): 3416, 1608, 1510, 1294 cm$^{-1}$

NMR (DMSO-d$_6$) δ: 7.9–8.1 (d, Ph, 1H), 7.2–7.4 (dd, Ph, 1H), 6.8–7.1 (m, Ph, 1H)

EXAMPLE 7

Preparation of 3-Methyl-4-Nitrophenol a) Esterification 10.94 g (0.1 mol) of m-cresol and 60 ml of ethyl acetate were put in a four-necked vessel having 100 ml capacity and mixed therein. To this mixture 22.3 ml (0.14 mol) of triethylamine was added under nitrogen gas atmosphere and ice-cooling. Then 10.15 g (80 mmol) of oxalyl chloride was added dropwise at 5° C., and the reaction mixture was warmed to a room temperature. The resulting precipitate was collected by filtration, washed with water and ethyl acetate to remove triethylamine hydrochloride, and dried in vaccum to give 3.0 g of bis(3-methylphenyl) oxalate as light brown crystals. On the other hand, the ethyl acetate layer was separated from the filtrate, then washed and dried. The solvent was removed in vacuum and the residue was washed with methanol to remove the starting material, i.e., m-cresol, and dried to give 5.71 g of bis(3-methylphenyl) oxalate. Total amount: 8.71 g (yield: 63.7%). m.p.: 101°–103° C.

b) Nitration and Hydrolysis 6 ml of concentrated sulfuric acid was put in a four-necked vessel having 50 ml capacity and ice-cooled. Then 1.51 g (5.88 mmol) of bis(3-methylphenyl) oxalate obtained above was added at 5° C. To this solution a mixture of 2.25 g of concentrated sulfuric acid and 2.08 g (2 eq. mol) of nitric acid (d=1.42) was added dropwise at 0° C. The reaction mixture was suspended in 20 g of ice and the resulting precipitate was collected. The precipitate thus obtained was suspended in 20 ml of methanol, and the pH of the solution was adjusted to 12 with a 35% sodium hydroxide solution and then to pH 4 with concentrated hydrochloric acid. The solution was extracted with ethyl acetate and the organic layer was dried and then removed in vacuum to give 1.43 g (apparent yield: 64.4%) of crude product.

The HPLC peak area ratio of the isomers in the crude product was as follows:

3-methyl-4-nitrophenol: 5.0%

2,4-dinitro-5-methylphenol: 95.0%

The above step of nitration and hydrolysis was repeated by using 0.05 g of bis(3-methylphenyl) oxalate. This time the nitration reaction was carried out at −5° C. to 0° C., and the amount of nitric acid used was 1 eq. mol. Thus 3.01 g of crude product was obtained (apparent yield: 50.6%).

The HPLC peak area ratio of the isomers in the crude product was as follows:

3-methyl-4-nitrophenol: 30.9%

2,4-dinitro-5-methylphenol: 64.0% m-cresol 0.4%

5-methyl-2-nitrophenol 4.7%

This crude product was purified by silica gel column chromatography (toluene/ethyl acetate=3:2) and recrystallized from water to give 3-methyl-4-nitrophenol. m.p.: 129° C.

COMPARATIVE EXAMPLE

Preparation of 4-Nitrophenol a) Esterification 10.57 g (0.11 mol) of phenol was dissolved in 60 ml of ethyl acetate in a four-necked vessel having 100 ml capacity. Under nitrogen gas atmosphere and ice-cooling, 21.4 ml (0.07 mol) of triethylamine was added at 5° C., and then 8.38 g (0.07 mol) of oxalyl chloride was added dropwise at the same temperature. Then the disappearance of the phenol was confirmed by thin-layer chromatography. The resulting precipitate was collected by filtration, washed with water and ethyl acetate to remove triethylamine hydrochloride, and dried in vacuum at 70° C. to give 8.00 g (60.9%) of diphenyl oxalate as a brown solid. m.p.: 129°–135° C.

b) Nitration and Hydrolysis 16 ml of concentrated sulfuric acid was put in a four-necked vessel having 100 ml capacity and ice-cooled. Then 4.18 g (17.26 mmol) of diphenyl oxalate obtained above was added at 5° C. To this solution a mixture of 6.96 g of concentrated sulfuric acid and 6.21 g of nitric acid (d=1.42) was added dropwise at the same temperature, and the reaction mixture was suspended in 40 g of ice water. By filtration and washing with water, a light brown precipitate was obtained. The precipitate was suspended in 20 ml of water, and a 35% of sodium hydroxide solution was added until the precipitate was dissolved. Then the pH of the solution was adjusted to 4 with hydrochloric acid. After extraction with ethyl acetate and drying over magnesium sulfate, the solvent was removed in vacuum to give 3.2 g (yield: 66.7%) of crude product.

The HPLC peak area ratio of the isomers in the crude products was as follows:

4-nitrophenol: 73.1%

2-nitrophenol: 8.4%

2,4-dinitrophenol: 18.5%

The peak of each isomer in the chromatogram was identified by using commercially available products.

What is claimed is:

1. A process for preparing a 4-nitrophenol derivative represented by the following formula (IV):

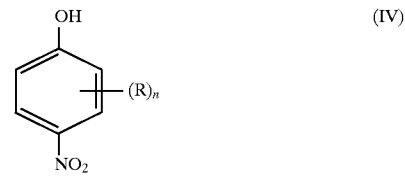

wherein R is, the same or different from each other, an alkyl group having 1 to 4 carbon atoms; a halogen atom; an alkoxy group having 1 to 4 carbon atoms; a formyl group; a nitrile group; —COOR$^1$ (R$^1$ is an alkyl group having 1 to 4 carbon atoms); —CONR$^2$R$^3$ (R$^2$ and R$^3$ are, the same or different from each other, hydrogen atom(s) or alkyl group(s) having 1 to 4 carbon atoms); or —COR$^4$ (R$^4$ is an alkyl group having 1 to 4 carbon atoms), and R is not substituted at the 4-position of the phenyl ring and not substituted at the 2- and 6-positions of the phenyl ring at the same time, and, n is 1, 2 or 3, by selective nitration procedure which comprises:

(A) reacting a phenol derivative of the following formula (I):

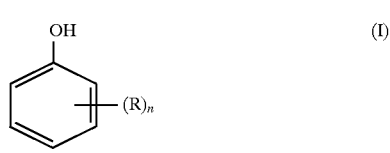

wherein R and n have the same meanings as above, with an oxalyl halide to give a diphenyl oxalate derivative of the following formula (II):

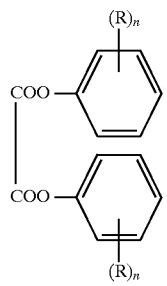

wherein R and n have the same meanings as above,
(B) nitrating the derivative of formula (II) with a mixture of concentrated sulfuric acid and nitric acid to give a bis(4-nitrophenyl) oxalate derivative of the following formula (III):

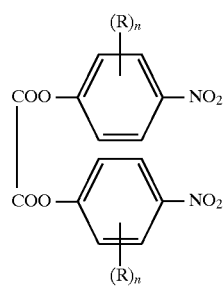

wherein R and n have the same meanings as above, and
(C) hydrolyzing the derivative of formula (III) to give said 4-nitrophenol derivative of formula (IV).

2. A process for preparing a 4-nitrophenol derivative represented by the following formula (IV):

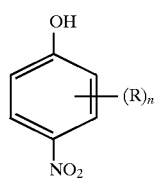

wherein R is, the same or different from each other, an alkyl group having 1 to 4 carbon atoms; a halogen atom; an alkoxy group having 1 to 4 carbon atoms; a formyl group; a nitrile group; —COOR$^1$ (R$^1$ is an alkyl group having 1 to 4 carbon atoms); —CONR$^2$R$^3$ (R$^2$ and R$^3$ are, the same or different from each other, hydrogen atom(s) or alkyl group(s) having 1 to 4 carbon atoms); or —COR$^4$ (R$^4$ is an alkyl group having 1 to 4 carbon atoms), and R is not substituted at the 4-position of the phenyl ring and not substituted at the 2- and 6-positions of the phenyl ring at the same time, and, n is 1, 2 or 3, by selective nitration procedure which comprises:
(A) reacting a phenol derivative of the following formula (I):

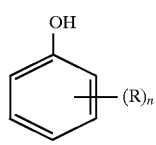

wherein R and n have the same meanings as above, with an oxalyl halide to give a diphenyl oxalate derivative of the following formula (II):

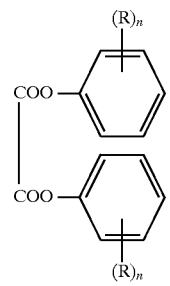

wherein R and n have the same meanings as above;
(B) nitrating the derivative of formula (II) to give a bis(4-nitrophenyl) oxalate derivative of the following formula (III):

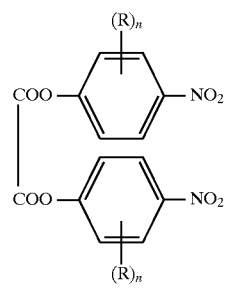

wherein R and n have the same meanings as above; and
(C) hydrolyzing the derivative of formula (III) to give said 4-nitrophenol derivative of formula (IV).

3. The process of claim 2 wherein the diphenyl oxalate derivative of formula (II) is nitrated with a reagent selected from the group consisting of a mixture of concentrated sulfuric acid and nitric acid, nitric acid, fuming nitric acid, an alkali metal salt of nitric acid in concentrated sulfuric acid, nitrous acetyl, a nitronium salt, and nitric oxide.

4. A process for preparing a 4-nitrophenol derivative represented by the following formula (IV):

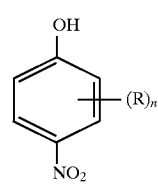

wherein R is, the same or different from each other, an alkyl group having 1 to 4 carbon atoms; a halogen atom; an alkoxy group having 1 to 4 carbon atoms; a formyl group; a nitrile group; —COOR$^1$ (R$^1$ is an alkyl group having 1 to 4 carbon atoms); —CONR$^2$R$^3$ (R$^2$ and R$^3$ are, the same or different from each other, hydrogen atom(s) or alkyl group(s) having 1 to 4 carbon atoms); or —COR$^4$ (R$^4$ is an alkyl group having 1 to 4 carbon atoms), and R is not substituted at the 4-position of the phenyl ring and not substituted at the 2- and 6-positions of the phenyl ring at the same time, and, n is 1, 2 or 3, by selective nitration procedure which comprises:

(A) reacting a phenol derivative of the following formula (I):

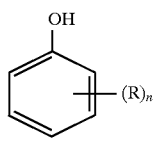

wherein R and n have the same meanings as above, with oxalic acid or a reactive derivative thereof, to give a diphenyl oxalate derivative of the following formula (II):

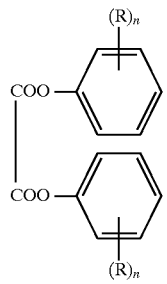

wherein R and n have the same meanings as above;

(B) nitrating the derivative of formula (II) with a reagent selected from the group consisting of a mixture of concentrated sulfuric acid and nitric acid, nitric acid, an alkali metal salt of nitric acid in concentrated sulfuric acid, nitrous acetyl, a nitronium salt, and nitric oxide to give a bis(4-nitrophenyl) oxalate derivative of the following formula (III):

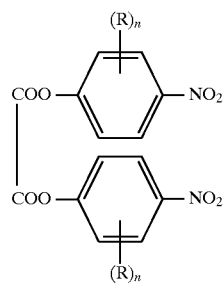

wherein R and n have the same meanings as above; and
(C) hydrolyzing the derivative of formula (III) to give said 4-nitrophenol derivative of formula (IV).

5. The process of claim 4 wherein the phenol derivative of formula (I) is reacted with an oxalyl halide to give the diphenyl oxalate derivative of formula (II).

6. The process of claim 4 wherein the diphenyl oxalate derivative of formula (II) is nitrated with a mixture of concentrated sulfuric acid and nitric acid.

7. The process of claim 4 wherein the diphenyl oxalate derivative of formula (II) is nitrated with nitric acid.

8. The process of claim 4 wherein the diphenyl oxalate derivative of formula (II) is nitrated with an alkali metal salt of nitric acid in concentrated sulfuric acid.

9. The process of claim 4 wherein the diphenyl oxalate derivative of formula (II) is nitrated with nitrous acetyl.

10. The process of claim 4 wherein the diphenyl oxalate derivative of formula (II) is nitrated with nitric oxide.

11. A process for preparing a 4-nitrophenol derivative represented by the following formula (IV):

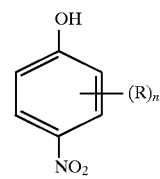

wherein R is, the same or different from each other, an alkyl group having 1 to 4 carbon atoms; a halogen atom; an alkoxy group having 1 to 4 carbon atoms; a formyl group; a nitrile group; —$COOR^1$ ($R^1$ is an alkyl group having 1 to 4 carbon atoms); —$CONR^2R^3$ ($R^2$ and $R^3$ are, the same or different from each other, hydrogen atom(s) or alkyl group(s) having 1 to 4 carbon atoms); or —$COR^4$ ($R^4$ is an alkyl group having 1 to 4 carbon atoms), and R is not substituted at the 4-position of the phenyl ring and not substituted at the 2- and 6-positions of the phenyl ring at the same time, and, n is 1, 2 or 3, by selective nitration procedure which comprises:
(A) reacting a phenol derivative of the following formula (1):

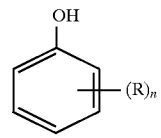

wherein R and n have the same meanings as above,
with oxalic acid or a reactive derivative thereof, to give a diphenyl oxalate derivative of the following formula (II):

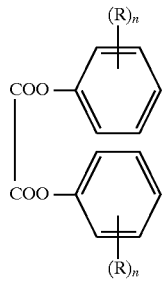

wherein R and n have the same meanings as above;
(B) nitrating the derivative of formula (II) to give a bis(4-nitrophenyl) oxalate derivative of the following formula (III):

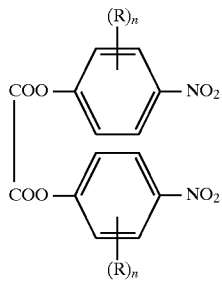

wherein R and n have the same meanings as above; and
(C) hydrolyzing the derivative of formula (III) with an alcohol to give said 4-nitrophenol derivative of formula (IV).

12. The process of claim 11 wherein the derivative of formula (III) is hydrolyzed with an alcohol selected from the group consisting of methanol, ethanol, and isopropanol.

13. The process of claim 11 wherein the phenol derivative of formula (I) is reacted with an oxalyl halide to give the diphenyl oxalate derivative of formula (II).

14. The process of claim 11 wherein the diphenyl oxalate derivative of formula (II) is nitrated with a reagent selected from the group consisting of a mixture of concentrated sulfuric acid and nitric acid, nitric acid, fuming nitric acid, an alkali metal salt of nitric acid in concentrated sulfuric acid, nitrous acetyl, a nitronium salt, and nitric oxide.

* * * * *